United States Patent [19]

Maget et al.

[11] Patent Number: 4,902,278
[45] Date of Patent: Feb. 20, 1990

[54] FLUID DELIVERY MICROPUMP

[75] Inventors: Henri J. R. Maget, Los Altos; Paul K. Krejci, San Diego, both of Calif.

[73] Assignee: IVAC Corporation, San Diego, Calif.

[21] Appl. No.: 16,019

[22] Filed: Feb. 18, 1987

[51] Int. Cl.⁴ .............................................. A61M 5/00
[52] U.S. Cl. ..................................... 604/132; 604/145; 604/891.1; 128/DIG. 12; 204/301; 429/27
[58] Field of Search ............... 604/892, 891, 151, 132, 604/145, 141; 128/DIG. 12; 417/472–473; 429/27; 204/180, 299, 301

[56] References Cited

U.S. PATENT DOCUMENTS

| | | | |
|---|---|---|---|
| 3,894,538 | 7/1975 | Richter | 204/301 X |
| 3,951,147 | 4/1976 | Tucker et al. | |
| 4,140,122 | 2/1979 | Kühl et al. | |
| 4,262,062 | 4/1981 | Zatsky | 429/27 |
| 4,340,048 | 7/1982 | Eckenhoff | |
| 4,402,817 | 9/1983 | Maget | |
| 4,505,701 | 3/1985 | Navato | |
| 4,525,164 | 6/1985 | Loeb et al. | |
| 4,552,561 | 11/1985 | Eckenhoff et al. | |
| 4,552,698 | 6/1985 | Maget | |
| 4,596,575 | 6/1986 | Rosenburg et al. | 604/891 |

Primary Examiner—Stephen C. Pellegrino

[57] ABSTRACT

A prime mover module used in a fluid delivery micropump, especially for pharmaceutical purposes, transports an electrochemically active material, such as oxygen, at a steady rate across an ion exchange cell to apply external pressure to a collapsible reservoir and expel fluid therefrom. An air-actuated battery, such as a zinc-air battery, which is located in the module in a fixed closed circuit with the cell and which shares one of its electrodes with the cell, is activated by peeling off an adhesive tape covering air inlet ports to thereby establish a voltage gradient acrosss the cell and control the rate at which fluid is expelled from the reservoir in accordance with the value of a resistor in the cell/battery circuit. The reservoir is filled or refilled by inserting a vented needle into an air bleed port while discharging a fluid-filled syringe inserted into a fluid injection port. Cylindrical and flat configurations, suitable for external use, operate on atmospheric oxygen, while an implantable configuration operates on oxygen from a self-contained reservoir.

21 Claims, 2 Drawing Sheets

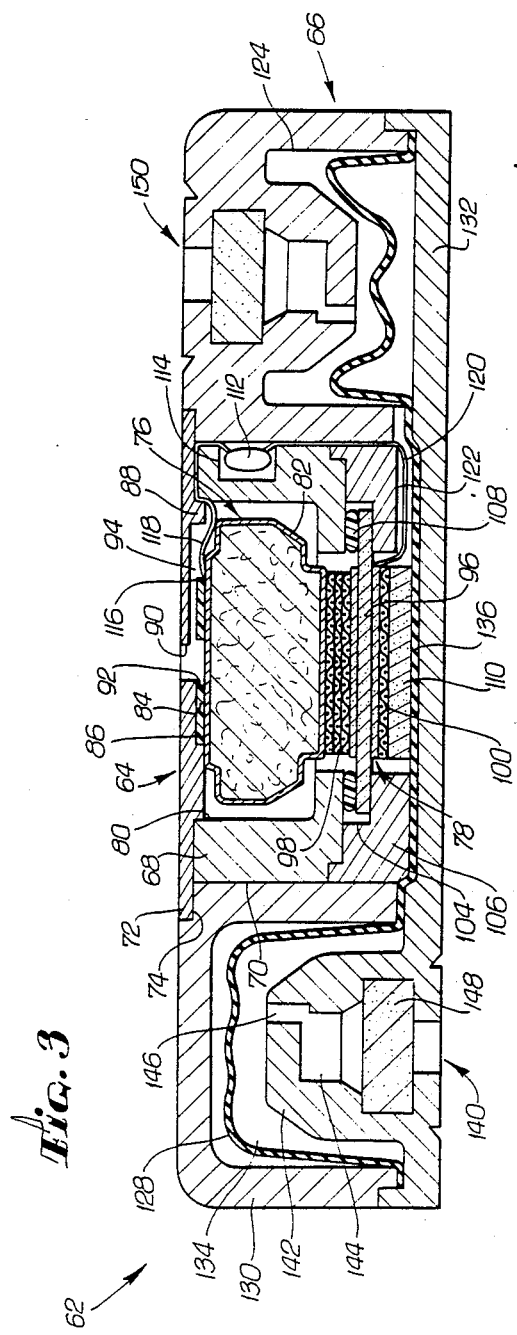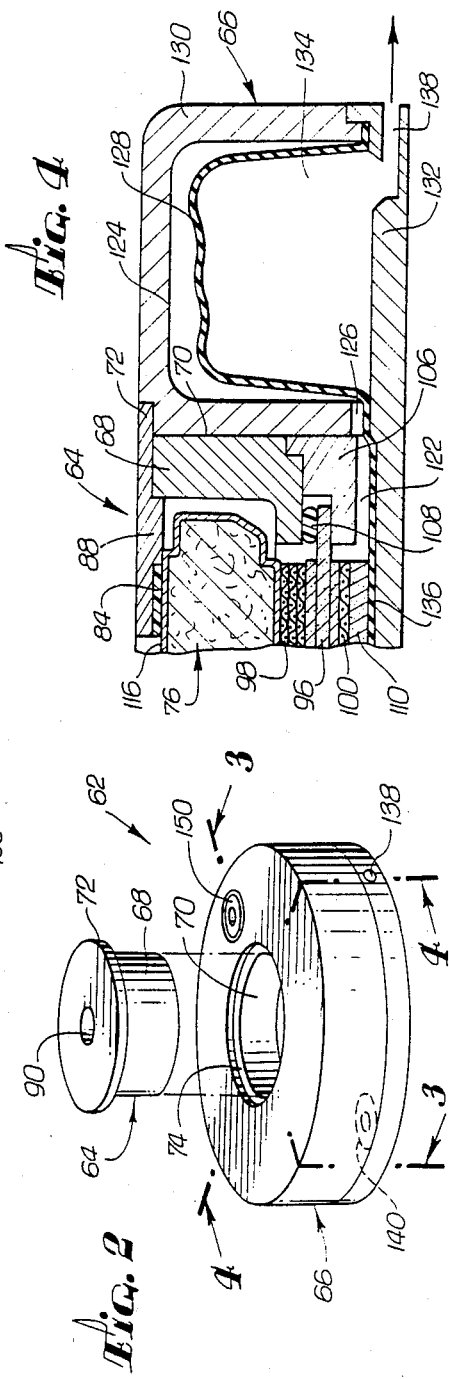

FLUID DELIVERY MICROPUMP

BACKGROUND OF THE INVENTION

This invention relates generally to prime movers and, more particularly, has reference to a new and improved prime mover module used in a fluid delivery micropump, especially for pharmaceutical applications.

In various clinical situations, the indicated procedure for treating the patient is to administer pharmaceutical fluids into his body at a sustained, very low rate over an extended period of time. Fluids administered in this manner include liquid nutrients, blood, plasma, insulin and hormones.

The traditional apparatus for the gradual administration of liquids into the human body is the intravenous administration set in which gravity induced hydrostatic infusion dispenses a drug from the familiar bottle suspended above the patient. Unfortunately, the IV set is not well-suited for use with an ambulatory patient.

Other methods for the gradual administration of drugs have been devised to eliminate the need for suspending the drug above the patient and thereby provide him with greater mobility. Mechanical pump dispensers use various types of mechanical pumps to expel the drug from a reservoir. Charged reservoir dispensers store a drug under pressure in a flexible reservoir and then selectively expel that drug by the force of internal reservoir pressure, the rate of release often being regulated by various valves. Pressurized gas dispensers use a pressurized gas to expel the drug. Osmotic dispensers rely on a solute that exhibits an osmotic pressure gradient against water to dispense the drug.

While the aforedescribed fluid administration techniques have served their purpose, there remains a continuing desire for further improvements therein.

When small quantities of drugs, such as hormones, are to be administered continuouly over a period of many hours, it is desirable to have a drug dispenser that is highly accurate and reliable, is sufficiently small and lightweight to be portable, and is convenient and easy to use. A copending patent application filed by Henri J. R. Maget, one of the instant inventors, entitled ELECTROCHEMICALLY DRIVEN DRUG DISPENSER, Ser. No. 729,860, filed May 2, 1985 now abandoned, discloses a drug delivery device which satisfies those needs. An electrochemical pump operating as a pressure source controls the delivery rate of small quantities of drugs. The pump is regulated by an external voltage supply and current controller.

The electrochemically driven drug dispenser disclosed in the above-mentioned patent application has many advantages, but additional improvements in the size, weight, cost, simplicity, flexibility and adaptability of drug dispensers are always desirable. A further need exists for a self-powered device which is compact, economical, simple in structure, and easy to operate, and which can be adapted to various applications requiring the gradual administration of drugs over an extended period of time. The present invention fulfills all of those needs.

SUMMARY OF THE INVENTION

Briefly, and in general terms, the present invention provides a self-powered, prime mover module which is compact, economical, simple in structure and easy to operate, and which is useful in a fluid delivery micropump adapted to deliver a substantially constant flow of fluid at relatively low rates. The invention is particularly well suited for an infusion pump which administers a gradual parenteral infusion of liquids, such as drugs or nutrients, into the body of a human or animal as a part of a medical procedure or treatment.

An infusion pump embodying features of the present invention is small and lightweight for use by an ambulatory patient who requires long-term treatment, e.g., a diabetic needing a continuous infusion of insulin. The pump has a simple structure, is easy to use, and inexpensive to manufacutre. It can be provided as a disposable unit, if desired.

In a presently preferred embodiment, by way of example and not necessarily by way of limitation, the prime mover module includes an electrochemical cell formed of an ion exchange membrane and two electrodes which draws a substantially steady flow of electrochemically active material, such as oxygen, from a reservoir or from the environment, and transfers it, via the ion exchange membrane, to an enclosed space surrounding a collapsible fluid reservoir. The pressure in the space compresses the reservoir to expel the fluid at a substantially constant flow rate. The expelled fluid passes through a tube connected to a venipuncture device, such as a needle or catheter, and is infused into the body of a patient.

The voltage gradient may be established across the electrochemical cell by a self-contained power source. In a particularly compact configuration, the self-contained power source shares one of its electrodes with the cell. The counter electrode evolves the electrochemically active material which is transferred across the ion exchange membrane. Small ports in the module direct the evolved material into the enclosed space surrounding the fluid reservoir.

In one embodiment of the invention, the power source is an air-actuated battery, such as zinc-air battery, which remains in a fixed closed circuit with the cell and produces electrical energy when exposed to air. The battery is activated by removing a protective peel tab to expose air inlet ports in one of the battery electrodes. Air invades the ports and reacts with the material in the battery core to produce a voltage across the battery. The electrochemically active material drawn in by the electrochemical cell enters through the ports. Use of an air-actuated battery in the manner described produces a self-powered module with an extremely long shelf life which has no on/off switches or other extraneous activation mechanisms.

A resistor in the circuit path between the power source and the electrochemical cell determines the amount of current through the cell which in turn determines the rate at which the electrochemically active material is transported across the membrane. The rate at which fluid is expelled from the reservoir is thus related to the value of the resistor and can be fixed by preselecting a particular resistance value or can be made variable by using a variable resistor or potentiometer. With a relatively constant voltage being provided by the power source, the resistor provides a substantially constant current across the membrane and the fluid is expelled from the reservoir at a substantially constant rate.

The fluid reservoir is pre-filled for one-time use or is provided with ports which allow the reservoir to be filled or re-filled as required. In one embodiment, the reservoir is filled by inserting a vented needle into an air bleed port while discharging a fluid-filled syringe inserted into an injection port. Preferably, the ports have sealable latex or gum rubber injection sites and are configured so that the inserted needles do not rupture the reservoir bladder.

The size, shape, geometry and aspect ratio of the device can be varied. The device can be configured for external use by operating on electrochemically active material taken from the environment or it can be configured for internal use, i.e., for implantation into the patient's body, by operating on electrochemically active material taken from a self-contained reservoir.

These and other objects and advantages of the invention will become apparent from the following more detailed description, when taken in conjunction with the accompanying drawings of illustrative embodiments.

DESCRIPTION OF THE DRAWINGS

FIG. 2 is a partially exploded, perspective view of another fluid delivery micropump embodying features of the present invention;

FIG. 3 is an enlarged, sectional view of the micropump shown in FIG. 2, taken substantially along the line 3—3;

FIG. 4 is an enlarged, fragmentary, sectional view of the micropump shown in FIG. 2, taken substantially along the line 4—4.

DETAILED DESCRIPTION OF THE PREFERRED EMBODIMENTS

Figure 1:
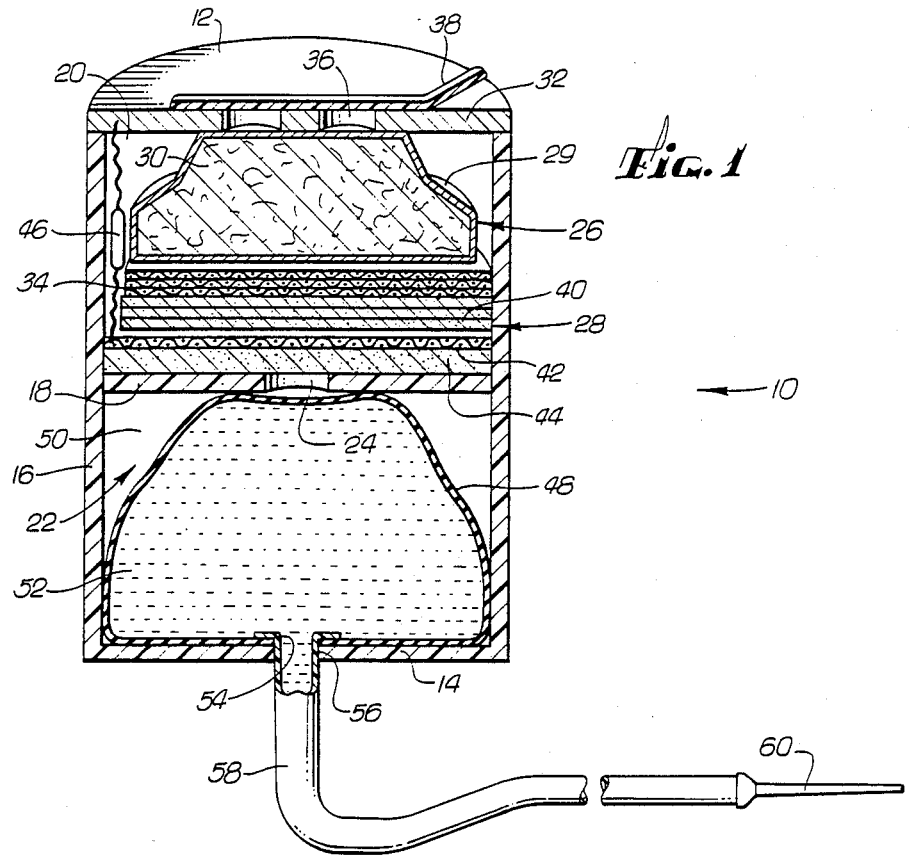
FIG. 1 is a perspective view, in section, of a fluid delivery micropump embodying features of the present invention.

As shown in the drawings for purposes of illustration, and with particular reference to FIG. 1, the present invention is embodied in a self-powered fluid delivery micropump, indicated generally by the numeral 10, which administers a gradual infusion of a drug or other liquid into the body of a patient at a relatively constant, low rate.

The pump housing has a pair of walls 12 and 14 sealed to the ends of a cylindrical body 16 to define a substantially gas-tight interior cylindrical cavity. The walls 12 and 14 and body 16 are preferably formed of gas impermeable plastic. A transverse interior wall 18 divides the cavity into a first zone 20 containing the prime mover and a second zone 22 containing the fluid reservoir. A central port 24 in the transverse wall 18 provides fluid communication between the zones 20 and 22.

The prime mover includes a battery, indicated generally by the numeral 26, and an electrochemical cell, indicated generally by the numeral 28. The battery 26 and cell 28 are both disposed within the pump housing.

The battery 26 has a casing 29 which surrounds a core 30 filled with a conventional power source material. The material undergoes a chemical reaction to convert chemical energy into electrical energy by processes well known in the art. The electrical energy produced by the source material is manifest as a voltage differential between a pair of electrodes 32 and 34 forming a part of the battery 26. In the illustrated embodiment, the outer electrode 32 serves as the cathode and the inner electrode 34 serves as the anode, although it will be appreciated by those skilled in the art that the polarity of the battery 26 may be reversed if necessary for certain applications.

The battery 26 can be one of various wellknown types of primary batteries, such as a mercury battery, manganese dioxide battery, aluminum-air battery or zinc-air battery. Air-actuated batteries, such as the aluminum-air battery or the zinc-air battery, or other batteries which produce power only when exposed to an activating agent, are preferred because they can be used without a mechanical or electrical on/off switch in the prime mover circuit. The zinc-air battery is the preferred battery 26 shown in the figures and the remainder of this specification will be directed to the structure and operation of devices incorporating that type of battery.

The outer electrode 32 is located adjacent the end wall 12 and may form a part thereof, if desired, as shown in the figure. A pair of air inlet ports 36 formed in the wall 12 and electrode 32 expose the battery core 30 to the ambient environment. Atmospheric air enters the ports 36 and reacts with the zinc in the core 30 to produce electrical energy in accordance with well known processes. To preserve the battery 26 when the pump is not in use, the ports 36 are sealed by a peelable protective tab 38, preferably adhesive tape, which is applied to the outer surface of the end wall 12 and extends across the ports 36. When the pump 10 is ready for use, the battery 26 is activated by peeling off the tab 38.

Although the preferred start/stop mechanism for the battery 26 is the port 36/peelable tab 38 combination described above, another mechanism or structure capable of selectively exposing or sealing the battery core 30 from the battery activating agent can be used. Moreover, the ambient environment need not necessarily be atmospheric air but can be another open or closed environment containing an activating agent compatible with the battery used in the pump 10. It will also be apparent that a mechanical or electrical switch or similar on/off device can be used as a primary or secondary start/stop mechanism, if desired.

The battery 26 applies a voltage across the electrochemical cell 28. The cell 28 includes an ion exchange electrolytic membrane 40, preferably a NAFION (perfluorosulfonic acid) membrane coated with platinum black/10% teflon, sandwiched between a pair of material-previous electrodes 34 and 42, preferably titanium screens or porous titanium disks. A particularly simple and compact structure is obtained by making one of the battery electrodes integral with one of the electrodes of the electrochemical cell. The term "integral with" is meant to encompass a single physical electrode shared by the battery 26 and cell 28, as shown in FIG. 1, or separate electrodes which effectively bear against each other or are in close proximity to each other.

Details of the structure and function of the electrochemical cell are set out in U.S. Pat. Nos. 4,402,817 and 4,522,698, entitled "Electrochemical Prime Mover" by Henri J. R. Maget, one of the co-inventors named herein. The entire disclosures of those patents are incorporated herein by reference and thus need not be extensively repeated here. Suffice it to say that the voltage gradient established across the electrochemical cell ionizes an electrochemically active material, such as the atmospheric oxygen entering the air inlet ports 36, at the electrode 34, transports the ions through the electrolytic membrane 40 to the other electrode 42, and reconverts the ions to molecules of the electrochemically active material which are evolved at the second electrode 42 into the region adjacent the internal wall 18. When the electrochemically active material is atmospheric oxygen or oxygen from some other source, the electrode 42 is conveniently called the oxygen evolution electrode. The water needed to support the action of the electrochemical cell (as described in the referenced U.S. Pat. No. 4,522,698) is supplied from a water-saturated cellulosic blotter 44 located between the oxygen evolution electrode 42 and the interior wall 18.

The electrochemical behavior of the prime mover module and the interaction between the battery 26 and the electrochemical cell 28 is characterized by the following reactions:

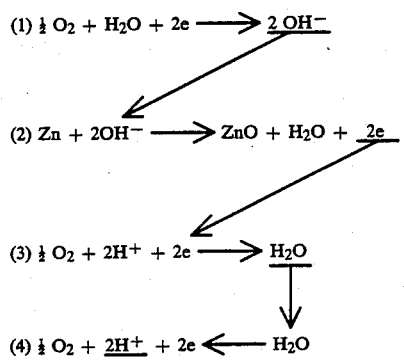

in which:

Reaction (1) occurs at the interface between the battery core 30 and the outer electrode 32;

Reaction (2) occurs at the interface between the battery case 29 and the electrode material internal to the shared electrode 34;

Reaction (3) occurs at the interface between the material external to the shared electrode 34 and the ion exchange membrane 40; and Reaction (4) occurs at the interface between the ion exchange membrane 40 and the oxygen evolution electrode 42.

The overall behavior of the prime mover module can be described as the sum of the battery 26 and cell 28 reactions as follows:

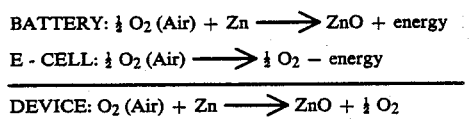

In the illustrated embodiment of the invention, the electrochemically active material drawn through the electrochemical cell 28 is also the activating agent for the battery 26, namely, the atmospheric oxygen entering the port 36. The oxygen reaches the cell 28 by passing through cavities or passageways in the zone 20 which by-pass the core 30. It is appreciated, however, that separate air inlet ports or other means may be provided for supplying atmospheric oxygen to the cell 28 independently of the supply to the battery 26. Moreover, it is appreciated that, in certain applications, it may be necessary or desirable to use an electrochemically active material differing from the battery activating agent, in which case separate inlet ports or other types of inlet arrangements may be required.

The battery 26/cell 28 circuit is completed by a resistor 46 which establishes electrical communication between the non-common electrodes 32 and 42 and which regulates the current developed in the module. The current is the physical mechanism which transfers the electrochemically active material across the ion exchange membrane 40. Hence, the rate of transfer is dependent upon the value of the resistor 46. Because the fluid delivery rate of the pump 10 is related to the rate at which the electrochemically active material is transferred across the membrane 40, the fluid delivery rate is controlled by selection of the resistor 46. For example, a prime mover module using a zinc-air battery (which produces a voltage of about 1.25–1.45 volts) and a resistor 46 of about 7,000 ohms could produce a fluid delivery rate of about 0.5 mL/day.

The pump 10 shown in FIG. 1 uses a fixed value resistor to deliver fluid at a substantially constant, fixed rate (assuming the use of a substantially constant voltage battery). That type of pump is preferred for applications requiring a universal flow rate because it is simple to manufacture and easy to use. However, for applications requiring changeable flow rates, the fixed resistor 46 may be replaced by a variable resistor or potentiometer to provide means for varing the delivery rate of the pump 10.

A collapsible reservoir 48, preferably formed by a pliable membrane or other elastomeric bladder material, is located in the fluid reservoir zone 22. The reservoir membrane acts as a displaceable barrier which separates the zone 22 into a gas chamber 50 and a liquid chamber 52. The gas chamber 50 communicates with the prime mover module via the port 24 in the interior wall 18. The reservoir 48 has an opening 54 which is sealed about a port 56 formed in the end wall 14 to establish communication between the liquid chamber 52 in the interior of the reservoir 48 and a fluid delivery line, such as a length of plastic tubing, connected to the port 56. The remote end of the fluid delivery line 58 is connected to a terminal device 60, which is a conventional venipuncture device, such as a catheter or needle, or is an adaptor suitable for connecting the line 58 to a separate venipuncture device.

When the tab 38 is removed, the battery 26 is activated and atmospheric oxygen is drawn into the housing, transferred across the electrochemical cell, and directed through the port 24 into the gas chamber 50. The resulting increase of pressure in the gas chamber 50 bears against the reservoir membrane which acts as a displaceable barrier between the gas chamber 50 and the liquid chamber 52. The reservoir 48 collapses under the pressure and urges the fluid in the liquid chamber 52 out the port 56 where it is delivered via line 58 to the terminal device 60 for infusion into the body of a patient under treatment.

Although the terminal device 60 has been described as a venipuncture device or adaptor thereto and the fluid contained in the reservoir 48 as a pharmaceutical fluid, it will be apparent that the pump 10 could be adapted for use in non-medical applications in which event different fluids and different terminal devices may be used.

The flow rate response of the pump 10 for a particular application can be readily determined. Assume that the terminal device 60 is a catheter of known geometry. For extremely small flow rates (Reynolds number well below 2,000), the pressure drop in the catheter can be calculated as follows:

$$\Delta P = bR = KRL/D^4$$

in which:
ΔP is the pressure drop in the catheter;
b is the hydrodynamic coefficient;
R is the fluid flow rate;
K is a quantity proportional to viscosity;
D is the diameter of the catheter; and
L is the length of the catheter.
Following a start-up transient defined by the following expressions:

$$R = R_{max}(1 - e^{-kt})$$

$$k = \frac{P_o}{bV_o}$$

in which:
t is time;
$P_o$ is the fluid delivery pressure; and
$V_o$ is the volume of the gas chamber above the fluid reservoir; the fluid flow rate reaches a maximum steady state level defined by the following expression:

$$R_{max} = \frac{P_o}{2b}\left\{\left(1 - \frac{4abI}{P_o^2}\right)^{\frac{1}{2}} - 1\right\}$$

in which:
a is the universal constant; and
I is the discharge current of the battery.

Accordingly, the start-up transient is an exponential function which is controlled by the delivery pressure and the initial gas volume and the steady state delivery rate can be calculated from known geometric parameters, the current and the universal constant.

It will be apparent to any person skilled in the art that the mechanism used to expel the fluid from the reservoir can be modified without departing from the present invention. The embodiment of the invention shown in FIGS. 2–4 illustrates one such modification.

The fluid delivery micropump 62 shown in FIGS. 2–4 is a small, lightweight and disposable embodiment of the invention which is particularly useful for providing a slow, continuous infusion of fluid into an ambulatory patient at a substantially constant rate and pressure. The flat, low-profile packaging makes it especially convenient for taping to a human arm or clipping to an animal's ear.

The micropump 62 has a two-part housing preferably formed of gas impermeable plastic. A central portion forms a prime mover module 64 and a peripheral portion circumferentially disposed about the central portion forms a fluid reservoir module 66. The prime mover module 64 has a cylindrical body 68 which is slideably received in a cylindrical cavity 70 in the center of the fluid reservoir module 66. An annular lip 72 extending from the outer end of the body 68 comes to rest upon an annular shoulder 74 on the outer end of the cavity 70 when the prime mover module 64 is properly positioned within the fluid reservoir module 66 so that the two modules 64 and 66 can be quickly and easily joined or separated. That feature makes the device especially economical because a single prime mover module 64 (which is generally the more expensive of the two modules) can be used with many different fluid reservoir modules 66. Similarly, should the battery become expended, a new prime mover module 64 can be used to continue operation of the micropump 62 with the same fluid reservoir module 66.

Apart from the differences in packaging which have been and will be pointed out, the prime mover module 64 is substantially identical in structure and function to the prime mover module 20 in the pump 10 shown in FIG. 1.

The module 64 includes a battery 76 and an electrochemical cell 78 located in an interior cavity 80 formed in the cylindrical body 68. The sides of the battery 76 are spaced inwardly from the wall of the cavity 80 and the battery is held in place by a silicone spacer 84 set in a groove 86 formed on the inner surface of a cap 88 which closes the outer end of the cylindrical body 68. An air inlet port 90 in the center of the cap 88 communicates with a central opening 92 in the spacer 84 to expose the battery 76 to the atmosphere. A portion of the air entering the port 90 is diverted around the battery 76 directly to the electrochemical cell 78 via a passageway 94 which passes between the outer surface 82 of the battery 76 and the wall of the cavity 80. The electrochemical cell 76 includes an ion exchange membrane 96, preferably a Nafion (perfluorosulfonic acid) membrane coated with platinum black/10% teflon, sandwiched between a shared electrode 98, preferably three superposed titanium screens, and an oxygen evolution electrode 100, preferably a single titanium screen. The periphery of the membrane 96 is received in an annular recess 104 formed in a base portion 106 of the cylindrical body 68 and is held in place by an annular silastic rubber spacer 108 also positioned in the recess 104. A water-saturated cellulosic blotter 110 is positioned between the inner electrode 100 and a central portion of the base 106. The cylindrical body 68 is connected to the cap 88 and to the base portion 106 by ultrasonic welds along the abutting surfaces.

A flow rate controlling resistor 112 located in a recess 114 on the outer surface of the cylindrical body 68 establishes a fixed closed circuit between the battery 76 and the electrochemical cell 78. The resistor 112 is connected to the battery cathode 116 by a first wire 118 which extends along the outer surface of the cylindrical body 68 and passes between the body 68 and the cap 88 into the passageway 94. The resistor 112 is connected to the oxygen evolution electrode 100 by a second wire 120 which extends along the outer surface of the cylindrical body 68 and through a radial groove 122 formed in the base portion 106 of the body 68. The groove 122 is one of a series of radial grooves formed in the base portion 106 to vent the oxygen produced at the oxygen evolution electrode 100 into the fluid reservoir module 66.

As best shown in FIGS. 3 and 4, the fluid reservoir module 66 has an internal annular cavity 124 which communicates with the oxygen outlet grooves 122 in the prime mover module 64 via a plurality of radial passageways 126 extending through the wall of the cylindrical cavity 70. A pliable bladder 128 extends around cavity 124 and has portions sealed between the body 130 and base 132 of the module 66 to define a substantially gas-tight, collapsible, annular fluid reservoir 134. For ease of manufacture and assembly, the bladder 128 is formed as a continuous element having a flat central portion 136 which extends between the base 106 of the prime mover module 64 and the base 132 of the fluid reservoir module 66.

In operation, oxygen drawn into the port 90 is transported across the ion exchange membrane 96 and evolved at the oxygen evolution electrode 100 in a manner identical to the pump 10 shown in FIG. 1. The evolved oxygen passes through the oxygen outlet grooves 122 and the radial passageways 126 to enter the cavity 124 where it applies pressure to the external surface of the bladder 128. The pressure collapses the reservoir 134, forcing the contained fluid through a radial outlet port 138 in the base 132 of the module 66. A conventional venipuncture device or other infusion device (not shown) may be connected to the outlet port 138 to administer the expelled fluid into the body of a patient in the manner described with reference to FIG. 1.

The reservoir 134 is filled through a fluid fill port, indicated generally by the reference numeral 140. The fill port 140 includes a rubber septum 148 sealed into the base 132 of the module 66 and a chamber wall 142 extending into the fluid reservoir 134. An offset axial bore 146 in the chamber wall 142 establishes communication between the fluid reservoir 134 and a central plenum chamber 144 in the wall 142 adjacent the septum 148. The septum 148 provides a resealable injection site 148, preferably formed of latex, gum rubber or some other resealable elastometric material. An air bleed port 150 of similar structure is provided on the opposite side of the module 66 in communication with the internal cavity 124.

To fill the reservoir 134, a vented needle (not shown) is inserted into the injection site in the bleed port 150 and the needle of a fluid-filled syringe (not shown) is inserted into the injection site 148 in the fill port 140. The offset bores are provided in the chamber walls so that the needles do not pass so far through the injection sites as to pierce the bladder 128. Fluid discharged from the syringe enters the reservoir 134, which expands to force air out the bleed port 150. The injection sites automatically reseal when the needles are removed so that the fluid remains in the reservoir 134.

The fill port and bleed port preferably include the septums described above in those applications where the reservoir 134 is filled by a syringe. Other types of port structures, such as luers, may be used in place of the septums in applications where other filling devices are used.

Figure 5:
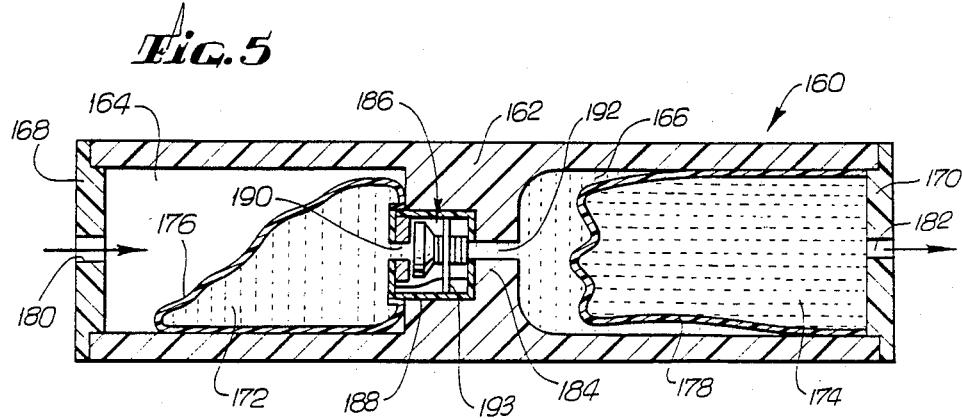
FIG. 5 is a sectional view of another embodiment of the invention in the form of an implantable fluid delivery micropump.

Referring to FIG. 5, another embodiment of the invention in the form of an implantable fluid delivery micropump is indicated generally by the numeral 160.

The pump 160 has a cylindrical housing 162 with interior lengthwise cylindrical cavities 164 and 166 adjacent each end. The cavities are closed by respective end caps 168 and 170.

A collapsible reservoir 172 containing electrochemically active material, such as oxygen, is located in one of the cavities 164 while a collapsible reservoir 174 containing the fluid to be pumped is located in the other cavity 166. The oxygen reservoir 172 is formed from a pliable membrane 176 whose edges are sealed along the inner end of the cavity 164. The fluid reservoir 174 is formed of a pliable membrane 178 whose edges are sealed along the outer end of the cavity 166 adjacent the end cap 170. An axial port 180 in one end cap 168 establishes communication between the environment and the portion of the cavity 164 external to the oxygen reservoir 172, while an axial port 182 in the other end cap 170 establishes communication between the environment and the interior of the fluid reservoir 174.

A central divider 184 extends across the housing 162 and separates the cavities 164 and 166. A prime mover module 186, substantially identical to the module 64 shown in FIG. 2, is received in a recess 188 formed in the surface of the divider 184 adjacent the oxygen reservoir 172. A port 190 in one end of the module 186 establishes communication between the interior of the module 186 and the interior of the oxygen reservoir 172. An axial passageway 192 in the divider 184 establishes communication between the opposite end of the module 186 and the portion of the cavity 166 external to the fluid reservoir 174. The ion exchange membrane 193 in the prime mover module 186 acts as a barrier between the cavities 164 and 166.

When the prime mover module 186 is activated, oxygen is drawn from the reservoir 172, which collapses under the pressure of ambient fluid entering the port 180 in the end cap 168. The oxygen is transported through the module 168 and expelled through the passageway 192 into the cavity 166. The fluid reservoir 174 collapses under the pressure of the oxygen in the cavity 166, forcing the fluid in the reservoir to be expelled out the port 182.

The pump 160 can operate in various environments because the electrochemically active material needed for the electrochemical cell and the activating agent needed for the battery are self-contained in an internal reservoir. Hence, the device 160 is particularly adaptable for implantation into the body of a patient.

In an alternative embodiment of the invention in the form of an implantable pump, the pliable membrane 176 forming the collapsible reservoir 172 for the electrochemically active material and the port 180 in the end cap 168 of the associated cavity 164 are eliminated. The cavity 164 is sealed and charged with the electrochemically active material. The prime mover module 186 draws that material from the sealed cavity with a resultant decrease in the internal pressure.

The prime mover module in any of the above described embodiments of the invention can be modified by choking the inlet ports 36, 90 and 190 to restrict or regulate the rate of intake of the electrochemically active material into the module. Regulating the intake of the electrochemically active material in that manner regulates the amount of current developed in the module and thus controls the fluid delivery rate. The current control resistor can be replaced by a short circuit, e.g. a length of wire, so that the current control function would be provided mechanically by the choked ports rather than electrically as previously described.

The choking is accomplished in one embodiment of the invention by reducing the diameter of the port to relatively small sizes. In an alternative embodiment of the invention, the choking is accomplished by a permeable membrane, e.g. an oxygen-permeable membrane such as silicone, which covers the port or is incorporated into the port. An additional advantage of using the membrane is that the module can be immersed in liquids which contain electrochemically active material. Such liquids would include body fluids, for example.

From the foregoing, it will be appreciated that the self-powered prime mover module of the present invention is compact, economical, simple in structure and easy to use and is readily adaptable to various applications where it is necessary to administer drugs to a patient at a substantially constant low rate over an extended period of time.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. A prime move module, comprising:
   a housing:
   means for introducing an electrochemically active material into said housing from a first region;
   an electrolytic membrane disposed in said housing and having first and second membrane surfaces;
   a first material-pervious electrode disposed on said first membrane surface and a second material-pervious electrode disposed on said second membrane surface; and
   an electrical power source disposed in said housing and having a pair of electrodes, one of said power source electrodes being integral with said first material-pervious electrode and having electrical communication means disposed within said housing for providing electrical communication between the other of said power source electrodes and said second material-pervious electrode, for establishing a voltage gradient across said electrolytic membrane to ionize said electrochemically active material at said first material-pervious electrode, transport said ions through said electrolytic membrane to said second material-pervious electrode, and reconvert said ions to molecules of said electrochemically active material which are evolved at said second material-pervious electrode into a second region, said power source including power source material that undergoes a chemical reaction which converts chemical energy into electrical energy when said power source material is exposed to said electrochemically active material.

2. Apparatus as set forth in claim 1, wherein said electrochemically active material comprises oxygen and said means for introducing said oxygen into said housing comprises at least one port formed in said housing to establish communication between the interior of said housing and an oxygen-containing environment in said first region.

3. Apparatus as set forth in claim 1, wherein said electrical communication means includes a registor.

4. Apparatus as set forth in claim 1, wherein said electrochemically active material comprises oxygen.

5. Apparatus as set forth in claim 1, wherein said electrical power source comprises a zinc-oxygen battery.

6. Apparatus as set forth in claim 1, wherein said other of the pair of electrodes is pervious to said electrochemically active material, thereby providing said means for introducing said electrochemically active material into said housing.

7. Fluid delivery apparatus, comprising:
   a prime mover module having a housing;
   means in said module for introducing electrochemically active material into said housing from a first region;
   an electrolytic membrane in said module disposed in said housing and having first and second membrane surfaces;
   a first material-pervious electrode disposed on said first membrane surface and a second material-pervious electrode disposed on said second membrane surface;
   means disposed within said housing of said module connected to said first and second electrodes for establishing a voltage gradient across said electrolytic membrane to ionize said electrochemically active material at said first material-pervious electrode, transport said ions through said electrolytic membrane to said second material-pervious electrode, and reconvert said ions to molecules of said electrochemically active material which are evolved at said second material-pervious electrode into a second region, said means including power source material that undergoes a chemical reaction which converts chemical energy into electrical energy when said power source material is exposed to said electrochemically active material;
   a fluid reservoir module having a housing adapted to receive said prime mover module;
   a collapsible reservoir disposed in said reservoir housing, said reservoir containing a fluid to be pumped and having an exterior surface adapted to be in communication with said second region when said prime mover module is received in said reservoir module;
   outlet means provided in said reservoir for permitting release of said fluid therefrom upon collapse of said reservoir, said reservoir being collapsed in response to pressure on said exterior surface caused by said evolution of material into said second region when said prime mover module is received in said reservoir module.

8. Apparatus as set forth in claim 7, wherein said first region comprises a reservoir in the prime mover module housing.

9. Apparatus as set forth in the claim 7, wherein said reservoir housing has a central portion and a peripheral portion having an internal annular cavity circumferentially disposed about said central portion, said prime mover module being disposed in said central portion and said collapsible reservoir being an annular reservoir disposed in said annular cavity, said reservoir housing further being provided with at least one passageway providing fluid communication between said central portion and annular cavity to enable said evolved electrochemically active material from said prime mover module to apply pressure to said exterior surface of said collapsible reservoir when said prime mover module is received in said reservoir module.

10. Apparatus as set forth in claim 9, wherein said prime mover module is selectively detachable from said peripheral portion of said housing.

11. A prime mover module, comprising:
    a housing;
    means for introducing electrochemically active material into said housing from a first region;
    an electrolytic membrane disposed in said housing and having first and second membrane surfaces;
    a first material-pervious electrode disposed on said first membrane surface and a second material-pervious electrode disposed on said second membrane surface;
    an electrical power source in a fixed closed circuit with said first and second electrodes for establishing a voltage gradient across said electrolytic membrane which ionizes said electrochemically active material at said first material-pervious electrode, transports said ions through said electrolytic membrane to said second material-pervious electrode, and reconverts said ions to molecules of said electrochemically active material which are evolved at said second material-pervious electrode into a second region, said fixed closed circuit being wholly disposed within said housing;

said electrical power source comprising power source material that undergoes a chemical reaction which converts chemical energy into electrical energy when said power source material is exposed to a activating agent; and wherein means are provided for selectively exposing said power source material to said activating agent.

12. Apparatus as set forth in claim 11, wherein said electrical power source further comprises a power source housing enclosing said power source material, and wherein said means for selectively exposing said power source material comprises at least one port formed in said power source housing to expose said power source material to an environment containing said activating agent and removable sealing means for closing said port.

13. Apparatus as set forth in claim 11, wherein said means for selectively exposing said power source material comprises regulator means for regulating said exposure of said power source material to said actuating agent.

14. Apparatus as set forth in claim 11, wherein said means for selectively exposing said power source material comprises at least one port formed in said power source housing, said port having a relatively small diameter which is selectively sized to regulate said exposure of said power source material to an environment containing said activating agent.

15. Apparatus as set forth in claim 11, wherein said means for selectively exposing said power source material comprises at least one port formed in said power source housing, said port being closed by a membrane which is impermeable to said activating agent, whereby said exposure of said power source material to said activating agent is regulated.

16. Fluid delivery apparatus, comprising:

a housing having a central portion and a peripheral portion with an internal annular cavity circumferentially disposed about said central portion;

means for introducing an electrochemically active material into said housing;

fluid pulp means disposed in said central portion for pressurizing a fluid, said fluid pump means including an electrolytic membrane disposed in said housing and having a first electrode and further including an electrical power source disposed in said housing and having a second electrode integral with said first electrode for establishing a voltage gradient across said electrolytic membrane, said electrical power source further comprising power source material that undergoes a chemical reaction which converts chemical energy into electrical energy when said power source material is exposed to said electrochemically active material;

an annular collapsible reservoir disposed in said cavity and containing a fluid to be pumped;

outlet means provided in said reservoir for permitting release of said fluid to be pumped upon collapse of said reservoir; and at least one passageway in said housing providing fluid communication between said fluid pump means and said cavity to apply pressurized fluid from said fluid pump means to the external surface of said collapsible reservoir, said reservoir being collapsed in response to said application of pressurized fluid.

17. Apparatus as set forth in claim 16, wherein said central portion of said housing is selectively detachable from said peripheral portion of said housing.

18. Apparatus as set forth in claim 16, wherein said housing is provided with a pair of closable port means, one of said port means being in communication with the interior of said collapsible reservoir to permit introduction of fluid therein and the other of said port means being communication with said cavity to permit venting of said cavity during said introduction of fluid into said reservoir.

19. A prime mover module, comprising:

a housing;

means for introducing an electrochemically active material into said housing;

an electrolytic membrane disposed in said housing, said membrane having a first and second membrane surfaces, a first membrane electrode disposed on said first membrane surface, and a second membrane electrode disposed on said second membrane surface;

an electrical power source disposed in said housing and including first and second power source electrodes, said second power source electrode being integral with said first membrane electrode, and including circuit means disposed within said housing for electrically communicating between said first power source electrode and said second membrane electrode, said power source including power source material that undergoes a chemical reaction which converts chemical energy into electrical energy when said power source material is exposed to said electrochemically active material.

20. The prime mover module of claim 19, wherein said first and second membrane electrodes are material-pervious electrodes.

21. The prime mover module of claim 19, wherein said circuit means includes a resistor.

* * * * *

UNITED STATES PATENT AND TRADEMARK OFFICE
CERTIFICATE OF CORRECTION

PATENT NO. : 4,902,278
DATED : February 20, 1990
INVENTOR(S) : Henri J. R. Maget et al.

It is certified that error appears in the above-identified patent and that said Letters Patent is hereby corrected as shown below:

Title Page:
In the Abstract, line 11, change "acrosss" to --across--.

Column 1, line 38, change "continuouly" to --continuously--.

Column 11, line 47 (claim 3, line 2) change "registor" to --resistor--.

Column 13, line 26 (claim 13, line 4), change "actuating" to --activating--.

Signed and Sealed this

Eleventh Day of August, 1992

Attest:

DOUGLAS B. COMER

*Attesting Officer*     *Acting Commissioner of Patents and Trademarks*